US008685318B2

(12) United States Patent
Collard et al.

(10) Patent No.: US 8,685,318 B2
(45) Date of Patent: Apr. 1, 2014

(54) APPARATUS FOR SANITIZING ORAL APPLIANCES

(76) Inventors: Glen Sheldon Gerald Collard, New Market (CA); Robert Michael Skinner, Mississauga (CA)

( * ) Notice: Subject to any disclaimer, the term of this patent is extended or adjusted under 35 U.S.C. 154(b) by 615 days.

(21) Appl. No.: 12/934,401

(22) PCT Filed: Mar. 25, 2009

(86) PCT No.: PCT/CA2009/000357

§ 371 (c)(1), (2), (4) Date: Sep. 24, 2010

(87) PCT Pub. No.: WO2009/117815

PCT Pub. Date: Oct. 1, 2009

(65) Prior Publication Data

US 2011/0020175 A1 Jan. 27, 2011

Related U.S. Application Data

(60) Provisional application No. 61/039,193, filed on Mar. 25, 2008.

(51) Int. Cl.

| | |
|---|---|
| ***A61L 2/00*** | (2006.01) |
| ***A61N 5/00*** | (2006.01) |
| ***A61B 18/18*** | (2006.01) |
| ***A61C 1/00*** | (2006.01) |

(52) U.S. Cl.

USPC ......... 422/24; 422/1; 250/455.11; 250/492.1; 607/94; 433/29; 606/3

(58) Field of Classification Search

USPC .................. 422/1, 22, 24; 250/455.11, 492.1; 607/88–91, 94; 433/29; 606/3

See application file for complete search history.

(56) References Cited

U.S. PATENT DOCUMENTS

| | | | | |
|---|---|---|---|---|
| 2,587,131 | A * | 2/1952 | Ficken | 250/455.11 |
| 4,806,770 | A | 2/1989 | Hylton et al. | |
| 5,029,252 | A * | 7/1991 | Ameseder | 250/455.11 |
| 5,547,635 | A | 8/1996 | Duthie, Jr. | |
| 6,753,537 | B2 | 6/2004 | Woo | |
| 7,560,706 | B1 * | 7/2009 | Castelluccio | 250/455.11 |
| 2007/0200072 | A1 | 8/2007 | Shin | |

* cited by examiner

*Primary Examiner* — Monzer R Chorbaji

(74) *Attorney, Agent, or Firm* — Miller Thomson LLP; Eduardo Krupnik

(57) ABSTRACT

An apparatus for sanitizing oral appliances is provided. The apparatus includes a housing movable between open and closed positions, at least one ultraviolet light source for emitting one or more sanitization means within the sanitizing chamber, and at least one power source for powering the ultraviolet light source. In the open position the housing allows insertion of the appliance, and in the closed position the housing defines a sanitizing chamber. The apparatus may include an appliance suspension system. The apparatus may include a reflective interior surface provided on at least a portion of the sanitizing chamber. The ultraviolet light source may be adapted to generate ozone within the sanitizing chamber. The apparatus may include control circuitry connecting the ultraviolet light source to the power source for the purpose of activating and deactivating the ultraviolet light source.

19 Claims, 14 Drawing Sheets

100
114
124
122
120
142b
112
142a
144
144
116

APPARATUS FOR SANITIZING ORAL APPLIANCES

CROSS REFERENCE TO RELATED APPLICATIONS

The present application is a national stage application under 35 U.S.C. 371 of PCT Application No. PCT/CA2009/000357 filed Mar. 25, 2009, which in turn claims the benefit under 35 U.S.C. 119(e) of U.S. Provisional Ser. No. 61/039,193, filed Mar. 25, 2008, the contents of each of which are hereby incorporated by reference into the present disclosure.

FIELD OF INVENTION

The invention relates in general to the field of apparatuses for sanitizing oral appliances.

BACKGROUND OF THE INVENTION

There is a need to sanitize items that collect significant amounts of bacteria, such as surgical instruments and oral appliances. Failure to sanitize such items allows bacteria to collect and to multiply upon the surface of such items. Future use of the bacteria infected items may cause illness and may pose a serious health risk. For this reason apparatuses for sanitizing items to kill bacteria collected on such items have been developed. The following patents disclose some of these types of apparatuses.

U.S. Pat. No. 5,029,252 (Ameseder) discloses an apparatus for disinfection of lavatory instruments, medical instruments or the like, through ultraviolet radiation, wherein the instruments are arranged within a housing in combination with a mounting plate and irradiated by a light source which generates UV-radiation.

U.S. Pat. No. 7,213,603 (Pinsky) discloses a system and method for toothbrush sanitization and storage whereby the bristles of a toothbrush may be inserted into a housing having a ultraviolet light for sanitizing the toothbrush bristles.

United States Patent Application No. 2006/0242788 (Day) discloses a portable, reusable cleansing system for mouth guards whereby a mouth guard may be inserted within a housing and an ultraviolet light may be utilized to sanitize the mouth guard.

SUMMARY OF THE INVENTION

The following is intended to introduce the reader to the invention but not to define or limit any claim. Inventions may reside in a combination or sub-combinations of the apparatus elements or process steps described below or in other parts of this document.

In one aspect, the present disclosure relates to an apparatus for sanitizing an oral appliance, characterized in that it comprises: a housing movable between open and closed positions, the housing in the open position allowing insertion of the oral appliance, the housing in the closed position defining a sanitizing chamber; an oral appliance suspension system; at least one ultraviolet light source capable of emitting one or more sanitization means within the sanitization chamber; and at least one power source for powering the at least one ultraviolet light source.

In another aspect, the present disclosure relates to an apparatus for sanitizing an oral appliance, characterized in that it comprises: a housing movable between open and closed positions, the housing in the open position allowing insertion of the appliance, the housing in the closed position defining a sanitizing chamber; an appliance suspension system; at least one ultraviolet light source capable of emitting one or more sanitization means within the sanitization chamber; at least one power source for powering the ultraviolet light source; and at least one reflective interior surface provided on or in the sanitizing chamber, whereby the one or more sanitization means may be reflected within the sanitizing chamber.

In yet another aspect, the present disclosure relates to an apparatus for sanitizing an oral appliance, the apparatus comprising: a housing movable between open and closed positions, the housing in the open position allowing insertion of the appliance, the housing in the closed position defining a sanitizing chamber; an ultraviolet light source disposed within the housing for emitting ultraviolet light and ozone gas within the sanitizing chamber; and at least one power source for powering the ultraviolet light source and the ozone source.

In another aspect, the present disclosure relates to a method of utilizing an apparatus to sanitize an oral appliance, characterized in that it comprises the steps of: manipulating a housing of the apparatus to an open position to facilitate access to an oral appliance suspension system; placing the oral appliance in the oral appliance suspension system; manipulating the housing of the apparatus to a closed position, whereby the oral appliance is positioned virtually centrally within a sanitization chamber that is defined within the housing when the apparatus is in the closed position; activating at least one ultraviolet light source to emit one or more sanitization means within the sanitization chamber; sanitizing the oral appliance by application of the sanitization means to the oral appliance; deactivating the at least one ultraviolet light source by one of the following: manipulating the housing of the apparatus to an open position; terminating a duration of a preset activation time; disengaging a manual switch connected to a control circuitry, whereby the at least one ultraviolet light source is deactivated; and disengaging a power source from providing power to the at least one ultraviolet light source.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The invention will be better understood and objects of the invention will become apparent when consideration is given to the following detailed description thereof. Such description makes reference to the annexed drawings wherein.

Figures 1A, 1B:
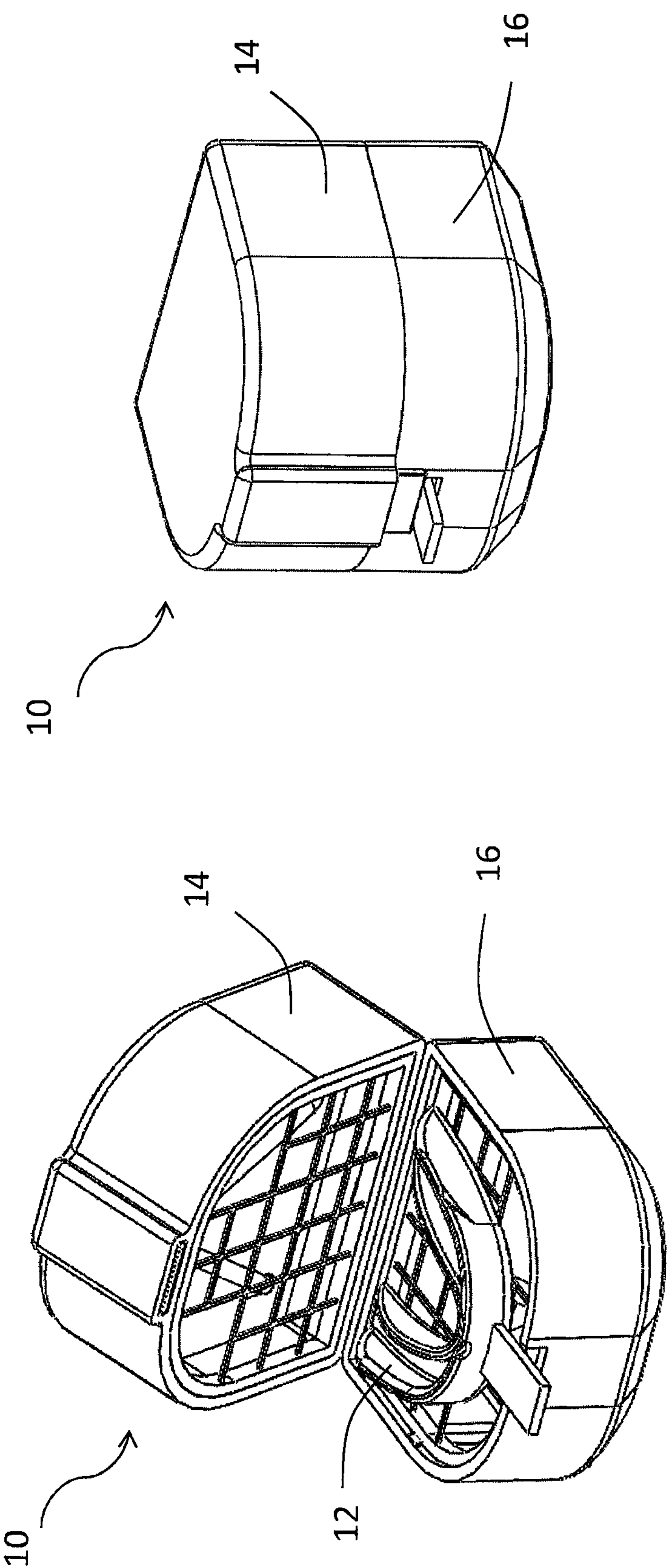
FIGS. 1A and 1B are perspective views of an apparatus in open and closed positions, respectively.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE INVENTION

Various apparatuses or methods will be described below to provide an example of embodiments of the present invention. No embodiment described below limits any claimed invention. The claimed inventions are not limited to apparatuses or methods having all of the features of any one apparatus or method described below or to features common to multiple or all of the apparatuses described below. It is possible that an apparatus or method described below is not an embodiment of any claimed invention. The applicant(s), inventor(s) and/or owner(s) reserve all rights in any invention disclosed in an apparatus or method described below that is not claimed in this document and do not abandon, disclaim or dedicate to the public any such invention by its disclosure in this document.

The present invention is an apparatus and method for sanitizing oral appliances. The apparatus may incorporate one or more sanitizing means, which may emit ozone gas and/or ultraviolet light, for the purpose of sanitizing the oral appliance. The apparatus may further incorporate a suspension means whereby the oral appliance may be positioned so that it does not contact the apparatus housing or other surfaces in the sanitation chamber. The suspension means may further facilitate virtually uninhibited access to the oral appliance by the sanitization means to ensure all over sanitization of the oral appliance. The method may pertain to steps to undertake sanitization of the oral appliance by application of the apparatus.

The present invention provides several benefits over the prior art. In particular, the suspension means positions the oral appliance in a manner that prevents it from making contact with the sanitization chamber walls or any other surface inside the chamber, including the light source, such as an ultraviolet light bulb or housing, no matter which angle the apparatus housing may be resting (e.g. on its side, on its top end, etc.). For example, when the apparatus is transferred from one location to another, such as within a carrying means, that may be a hockey bag, a athletic equipment bag, a school bag, a box, or any other carrying means, it is possible that the apparatus will rest on its side, or may even be moved about and caused to rest in many positions. Prior art apparatuses fail to prevent an instrument or appliance from coming into contact with the walls or other surfaces inside the apparatus if the apparatus is not sitting in a specific position. When an oral appliance is in contact with any of the walls or other surfaces, the contact prohibits the sanitization of the portion of the appliance that is in contact with the wall or other surface.

Bacteria may survive on the unsanitized portion of the appliance and may multiply, resulting in an appliance that is infected with bacteria. This diminishes the efficacy of the sanitization apparatus. The suspension means of the present invention prevents contact between the oral appliance and the sanitization chamber walls or other surfaces, no matter what angle the apparatus rests, to facilitate effective sanitization.

Another benefit is that embodiments of the present invention may utilize both ultraviolet light and ozone as sanitization means. Ultraviolet light may kill bacteria it contacts directly. Ozone gas may also kill bacteria. Certain ultraviolet lights may produce ozone gas, for example, such as ultraviolet lights at wavelengths between approximately 100 to 280 nanometers. Applying both ultraviolet light and ozone may result in a higher percentage of bacteria being killed than in prior art apparatuses and consequently may increase the effectiveness of the sanitization of the present invention apparatus.

A further benefit is that the ultraviolet light of the present invention may be shielded, so that the light source is protected from contact with the oral appliance, or other foreign items, including the fingers of a user. The shield may be formed of a variety of forms of barriers. The life and performance of an ultraviolet light may be significantly reduced when it is contacted by foreign items. The production of the ultraviolet light of the present invention may cause the light to perform at an its optimum level during the longest period it is able to do so. This may further reduce the cost of operating the apparatus as it lengthens the period before replacement of the ultraviolet light bulb is required.

Yet another benefit of the present invention is that the circuitry of the present invention may be designed to turn the ultraviolet light source off should the apparatus is opened while sanitization is underway. Ultraviolet light may be harmful to human eyes if it is looked at directly. Embodiments of the present invention that incorporate such a feature may protect the user from inadvertently harming themselves or others near the apparatus who may look at the ultraviolet light. Known prior art does not include this feature.

Referring to FIGS. 1A and 1B, an embodiment of the present invention is shown, including an apparatus indicated generally as 10. The apparatus 10 is shown in combination with an oral appliance 12. The oral appliance 12 may be, for example but is not limited to, a mouth guard, dentures, a retainer, a night guard, invisible braces, teeth whitening trays, etc. A skilled reader will recognize that a wide range of oral appliances may be sanitized by embodiments of the present invention. The apparatus may be formed of a variety of materials, including all types of plastic and metal materials. An embodiment may be formed of a lightweight, durable material, such as a plastic. A skilled reader will recognize that a wide range of materials may be utilized to form the apparatus.

The apparatus 10 includes a housing sized to receive the variety of types of appliances 12. Alternatively the housing may be sized to receive a specific type of appliance. As shown in FIGS. 1A and 1B, the housing may include an upper portion 14 and a lower portion 16. The upper portion 14 and the lower portion 16 may be movable to define an open position, as shown in FIG. 1A, and a closed position, as shown in FIG. 1B. In the open position, the housing may permit insertion and removal of the appliance 12. In the closed position, the housing may define a sanitizing chamber sized to receive one of a variety of types of appliances 12. Alternatively the sanitizing chamber may be sized to receive a specific type of appliance. The upper portion 14 and the lower portion 16 may be connected by a hinge (not shown). A detent or fastener may be provided for maintaining the upper and lower portions 14, 16 in the closed position (not shown).

Figure 2B:
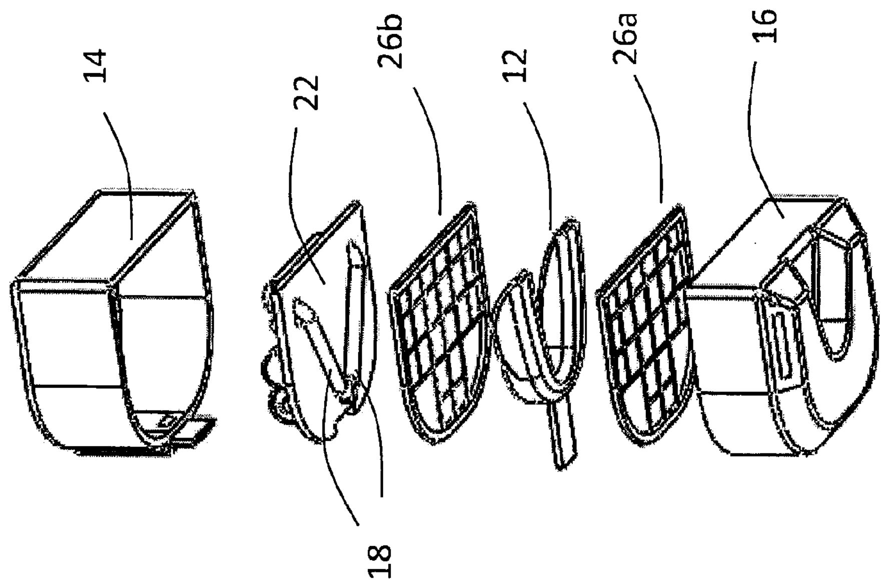
FIGS. 2A and 2B are exploded upper and lower perspective views of the apparatus shown in FIGS. 1A and 1B, respectively.
Figure 2A:
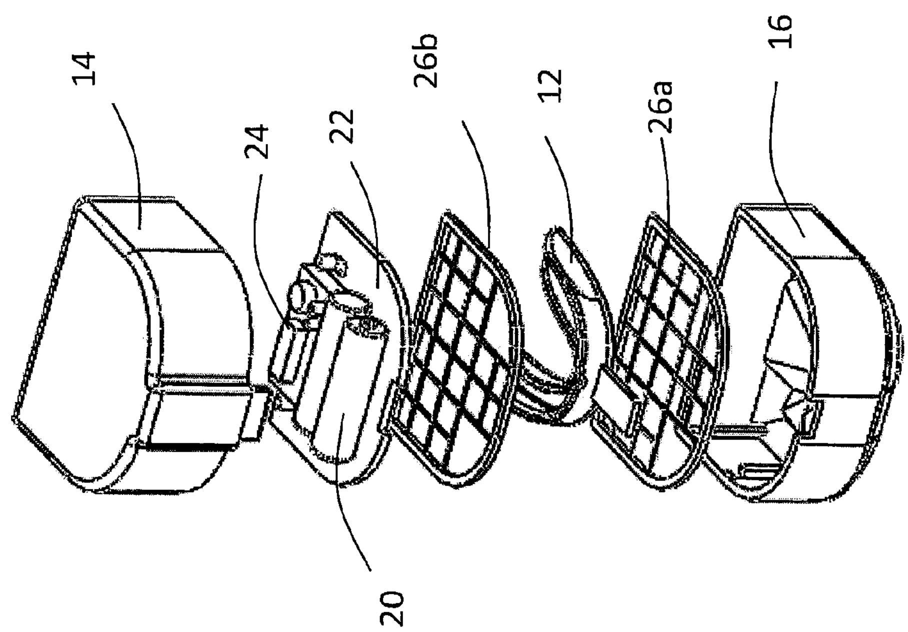

Referring to FIGS. 2A and 2B, the apparatus 10 includes at least one sanitization means source, such as an ultraviolet light source 18, for emitting ultraviolet light within the sanitizing chamber, and at least one power source 20 for powering the sanitization means source 18. The ultraviolet light source 18 may include, for example, one or more ultraviolet light bulbs. In particular, the ultraviolet light source 18 may include, for example, one or more UVC bulbs. In addition to emitting ultraviolet light, the ultraviolet light source may be adapted to generate ozone within the sanitizing chamber. For example, the ultraviolet light source 18 may be a UVC bulb operable to emit ultraviolet light and generate ozone within the sanitizing chamber. For example, the UVC bulb may be operable to emit ultraviolet light having a wavelength of about 100 to about 280 nanometers, or about 170 to about 260 nanometers, or about 175 to about 220 manometers, or about 180 to 190 nanometers. A skilled reader will recognize that sanitization means sources other than an ultraviolet light source may be applied in embodiments of the present invention, and that should an ultraviolet light source be applied, many forms of this type of source may be utilized in the present invention.

The ultraviolet light source 18 may be secured to the upper portion 14 of the apparatus 10. In particular, ultraviolet light source 18 may be secured to a divider 22 and the divider 22 may be secured to the upper portion 14. The sanitizing chamber may be defined by space between the divider 22 and the interior of portions 14, 16 that is accessible by ultraviolet light.

In one embodiment of the present invention, the ultraviolet light source may be shielded from contact with objects, such as the fingers of a user. The shield may be either a barrier erected to protect the ultraviolet light source, or a formation of the sanitization chamber that prevents access to the ultraviolet light source. For example, such as a transparent plastic cover fitted over the ultraviolet light source where such ultraviolet light sourced protrudes within the sanitization chamber. Alternatively the ultraviolet light source may be recessed within a wall of the sanitization chamber in a manner that causes it to be inaccessible by items, such as the oral appliance, fingers of a user, or other items that may from time to time be within the sanitization chamber. The shield may be formed so as to allow the light and ozone gas generated by the ultraviolet light source to be emitted within the sanitization chamber in a virtually unhindered manner. A skilled reader will recognize that a variety of shields may be formed and applied in the present invention.

The at least one power source 20 may be, for example, one or more batteries (as illustrated), or a plug for connection to a domestic power socket, or a solar panel (not shown), any combination thereof, or any other power source. If the power source 20 includes a battery, the apparatus 10 may further include a battery light (not shown) for indicating power status. A skilled reader will recognize that one or more indicators, being lights or other indicators, for example, such as an audible indicators, may be utilized in combination with other power sources to indicate when the power source is in use, depleted, or any other status of the power source.

The apparatus 10 may also include control circuitry 24 for electrically connecting the ultraviolet light source 18 to the power source 20. In an embodiment of the present invention, the power source 20 and the control circuitry may be disposed generally between the divider 22 and the upper portion 14. The ultraviolet light source 18 may be disposed on a side of the divider 22 opposing the power source 20 and the control circuitry 24, facing the sanitizing chamber.

The apparatus 10 may further include an appliance suspension system for suspending the appliance 12 within the sanitizing chamber. For example, the appliance suspension system may include at least a first platform 26*a* for holding the appliance 12 in a central position within the sanitizing chamber when the housing is in the closed position. The first platform 26*a* may include mesh-like structure having a substantially open surface to allow light and/or gas to pass therethrough. For example, the mesh-like structure may have more than 80% open space along a particular section, or more than 90% open space along a particular section. A skilled reader will recognize that the mesh-like structure may have many variations on the open space incorporated therein. The first platform 26*a* is adapted to hold the appliance 12 virtually centrally within the sanitizing chamber with minimal or little contact between the first platform 26*a* and the appliance 12. Minimal or little contact between the first platform 26*a* and the appliance 12 ensures adequate exposure of the appliance 12 to ultraviolet light and/or ozone emitted by the ultraviolet light source 18.

The appliance suspension system may also include a second platform 26*b* arranged on an opposite side of the appliance 12 from the first platform 26*a*. The platforms 26*a*, 26*b* may hold the appliance 12 in a virtually central position within the sanitizing chamber when the housing is in the closed position. Both platforms 26*a*, 26*b* may be seated in the lower and upper portions 16, 14, respectively, and may be removable from the housing to allow cleaning or replacement thereof. The second platform 26*b* may also include a mesh-like structure having a substantially open surface to allow light and/or gas to pass therethrough. For example, the mesh-like structure may have more than 80% open space along a particular section, or more than 90% open space along a particular section. A skilled reader will recognize that the mesh-like structure may have many variations on the open space incorporated therein. The platforms 26*a*, 26*b* may be adapted to hold the appliance 12 virtually centrally within the sanitizing chamber with minimal or little contact between the platforms 26*a*, 26*b* and the appliance 12. Minimal or little contact between the platforms 26*a*, 26*b* and the appliance 12 ensures adequate exposure of the appliance 12 to ultraviolet light and/or ozone gas emitted by the ultraviolet light source 18. The second platform 26*b* also serves to prevent the appliance 12 from making contact with the ultraviolet light source 18.

Figure 3B:
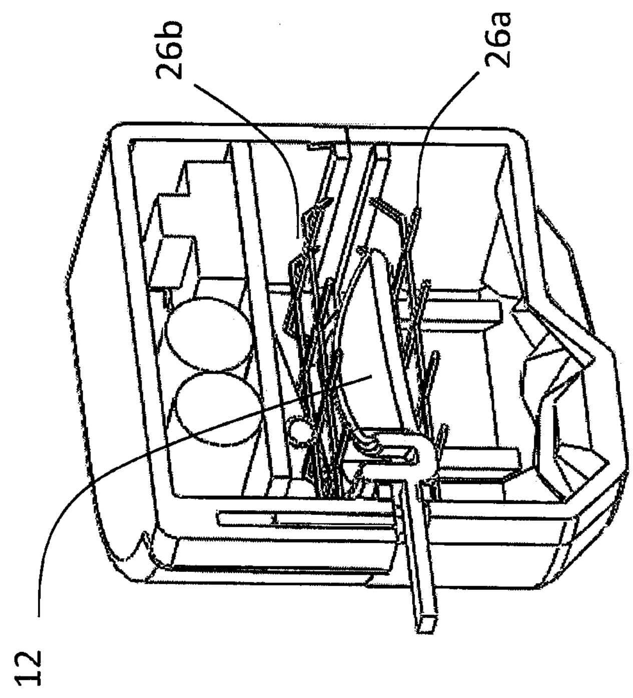
FIGS. 3A and 3B are sectional upper perspective views of the apparatus shown in FIGS. 1A and 1B in the closed position without and with an oral appliance, respectively.
Figure 3A:
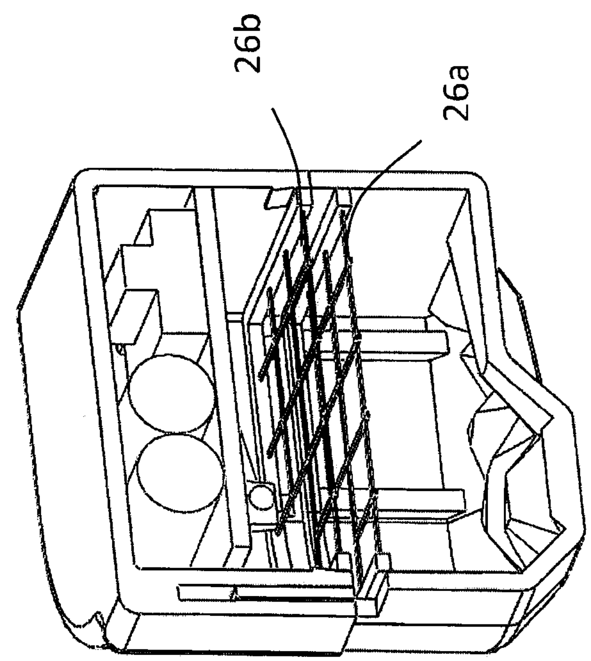

Referring to FIGS. 3A and 3B, at least one of the platforms 26*a*, 26*b* may be flexible for accommodating appliances of varying sizes. For example, the mesh-like structures of the first platform 26*a* and/or the second platform 26*b* may be formed of elastic members configured to resiliently deflect when an appliance 12 is inserted into the housing and the housing is closed. Alternatively, the mesh-like structure of the first platform 26*a* may be formed of elastic members configured to resiliently deflect when an appliance 12 is inserted into the housing and the housing is closed. The second platform 26*b* may be formed of a relatively firm material that does not deflect significantly. Formed of a relatively firm material, the second platform 26*b* may serve to prevent the appliance 12 from making contact with the ultraviolet light source 18. A skilled reader will recognize that a wide variety of materials may be utilized to form the first and second platforms to facilitate the function and purpose of these platforms.

Figure 13:
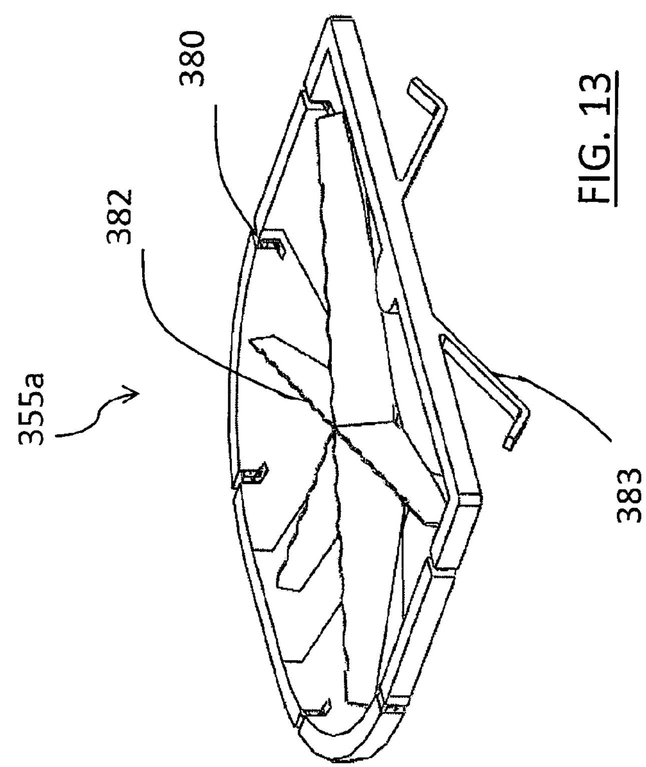
FIG. 13 is a perspective view of the lower tray of the apparatus.
Figure 12:
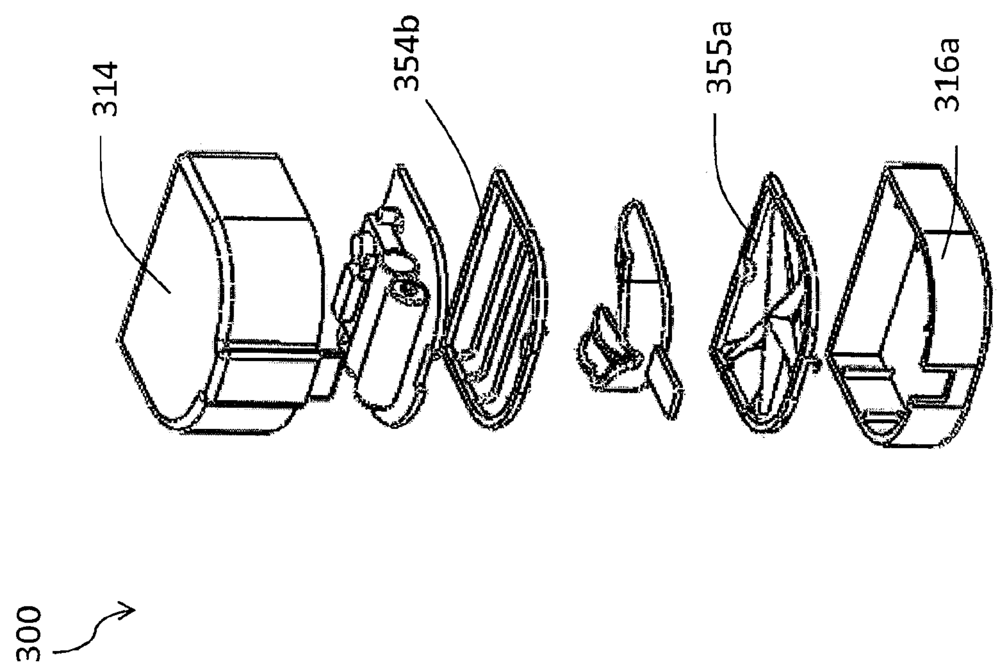
FIG. 12 is an exploded view of the apparatus.

In an embodiment of the present invention, as shown in FIG. 12, the first platform 355*a* may be included within an apparatus 300 and fitted inside a housing 314. The first platform 355*a* may be formed of a firm material, which may be the same material as the second platform 354*b* is formed of, or a material of relative firmness to that of the second platform. As shown in FIG. 13, the first platform may further be formed of a ridged material. In particular a riser 382 may be incorporated in the first platform that is formed of a ridged material. An oral appliance may be positioned upon the spacer so that the appliance is in minimal contact with the edges of the spacer, to allow maximum portions of the oral appliance to be reachable by the sanitization means. The ridged material of the spacer may further act to prevent sliding by the oral appliance and ensure the oral appliance is positioned virtually centrally within the sanitizing chamber and thereby does not make contact with the walls of the sanitizing chamber.

Figure 14B:
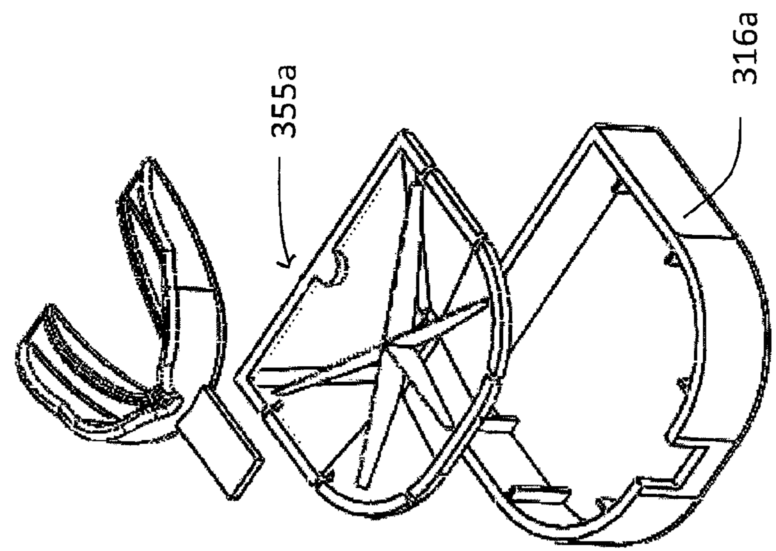
FIG. 14B is an exploded view of the lower portion of the apparatus.
Figure 14A:
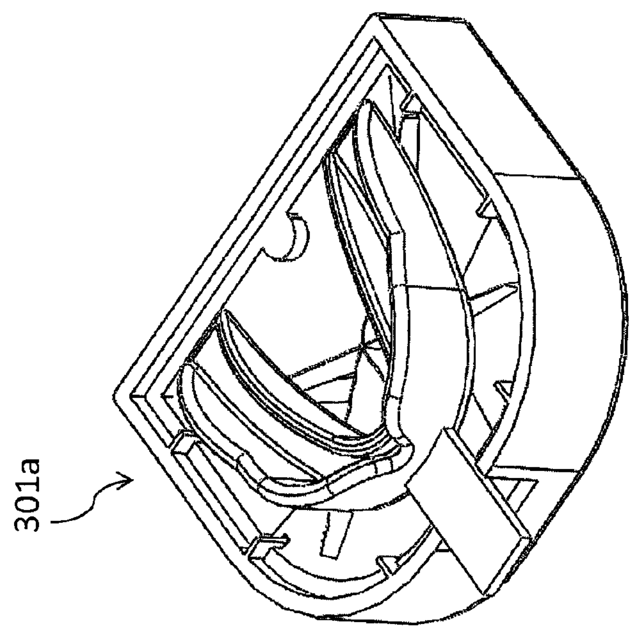
FIG. 14A is a perspective view of the lower portion of the apparatus with an oral appliance inserted therein.
Figure 15B:
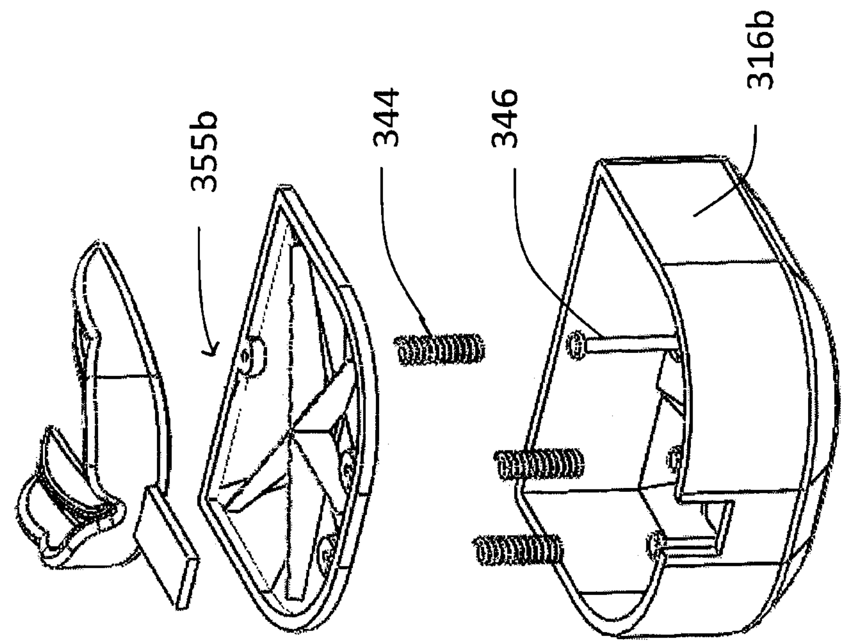
FIG. 15B is an exploded view of the lower portion of the apparatus.
Figure 15A:
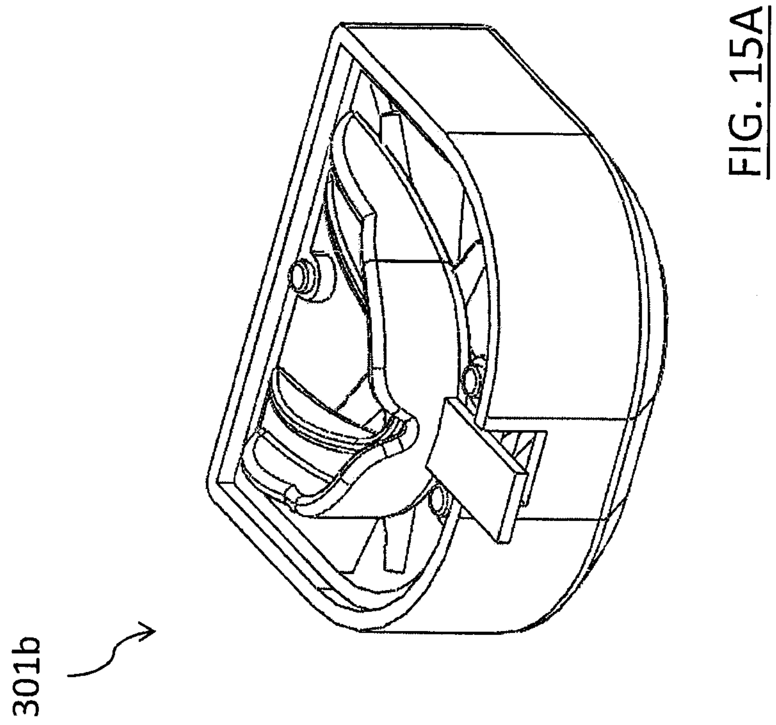
FIG. 15A is a perspective view of the lower portion of the apparatus with an oral appliance inserted therein.

The first platform may further incorporate one or more spacers 380 which may be depressions, indents, slots, protrusion or other means for the purpose of integration with structures, such as posts or other means, within the sanitizing chamber for the purpose of positioning the first platform within the sanitizing chamber. As shown in FIGS. 15A and 15B, an alternative embodiment of the present invention may incorporate one or more holes positioned to correspond to posts 346 in the lower portion 301*b* of the housing 316*b*. An attachment means, such as a screw, may be utilized to attach the first platform 355*b* to the lower portion 316*b* in a detachable manner when the holes are aligned with the posts and the attachment means is inserted through the hole and contacts the post. As shown in FIGS. 14A and 14B, spacers and the corresponding structures in the lower portion 301*a* of the sanitizing chamber may provide a means of preventing an oral appliance inserted upon the first platform 355*a* from resting against the walls of the sanitizing chamber or other surfaces within the housing 316.

Figure 4:
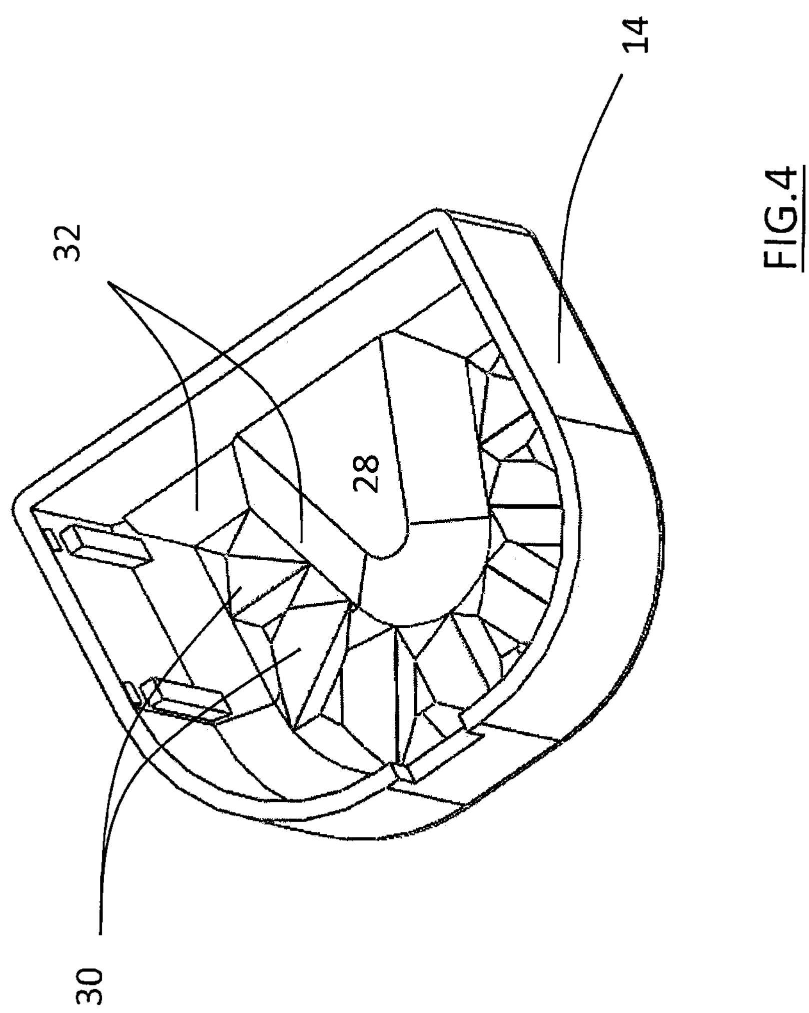
FIG. 4 is a upper perspective view of a lower portion of housing of the apparatus shown in FIGS. 1A and 1B.

Referring to FIG. 4, a reflective interior surface 28 may be provided on or in the sanitizing chamber. As shown in FIG. 4, the reflective interior surface 28 may be included along an interior surface of the lower portion 14 of the housing. The reflective interior surface 28 may be adapted to scatter light and/or ozone within the sanitizing chamber. For example, the reflective interior surface 28 may include polyhedral surfaces 30 adapted to scatter light, such as pyramidal or truncated pyramidal structures. The reflective interior surface 28 may also include curvilinear surfaces 32 adapted to scatter light. The reflective interior surface 28 may be provided on a tray that sits within the lower portion 14. The tray may be removable from the housing to allow for cleaning or replacement of the tray.

The apparatus may also include other reflective surfaces within the sanitizing chamber. The reflective interior surface may additionally be included along any or all of the side walls, top wall, surfaces of the sanitizing chamber, or stand within the chamber, to increase internal reflection. For example, the divider 22 may include a reflective interior surface proximate to the at least one ultraviolet light source 18 (see FIG. 2B), facing the sanitizing chamber and opposing the reflective interior surface 28. In addition, interior sidewall surfaces of the upper portion 14 and/or the lower portion 16 may also include reflective surfaces for reflecting/scattering light and ozone within the sanitizing chamber. A skilled reader will recognize the many and varied incorporations of reflective surfaces within the sanitization chamber that may be applied.

Figure 5:
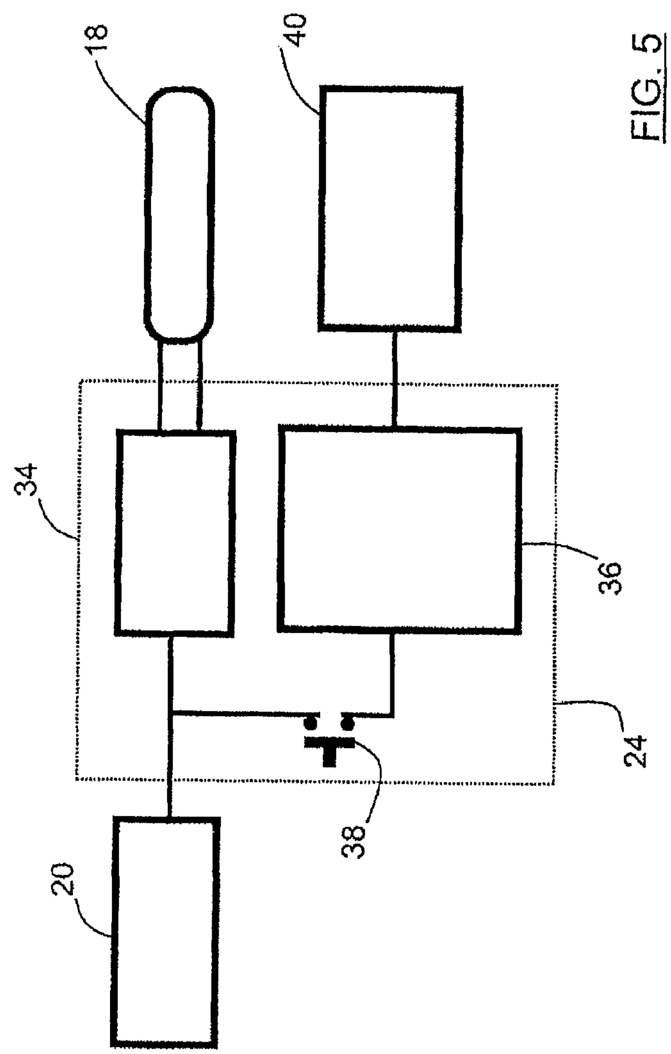
FIG. 5 is a schematic diagram.

Referring to FIG. 5, a schematic is provided. The control circuitry 24 electrically connects the at least one ultraviolet light source 18 to the at least one power source 20. The control circuitry 24 may include driver and/or ballast 34 configured to operate the at least one ultraviolet light source 18.

For an automatic "on" feature, the control circuitry 24 may also include a timer circuit 36 that is configured to connect the power source 20 to the ultraviolet light source 18 to activate the ultraviolet light source 18 when the housing transitions from the open position to the closed position. The timer circuit 36 may then disconnect the power source 20 from the ultraviolet light source 18 to deactivate the ultraviolet light source 18 after duration of an activation time. The activation time may be, for example, 5, 10 or 15 minutes, and may either be preset or selectable by the user using a switch (not shown). Optionally, as an automatic "shut-off" feature, the timer circuit 36 may also be configured to disconnect the power source 20 from the ultraviolet light source 18 to deactivate the ultraviolet light source 18 if the housing transitions from the closed position to the open position during the activation time.

The control circuitry 24 may further comprise a manual switch 38 for activating the ultraviolet light source 18, such that the control circuitry 24 connects the power source 20 to the ultraviolet light source 18 to activate the ultraviolet light source 18 if the housing is in the closed position and the manual switch 38 is engaged. The control circuitry 24 may also comprise a light or an audible indicator 40 for indicating if the ultraviolet light source 18 is activated and/or if the ultraviolet light source 18 transitions from activated to deactivated states. The control circuitry 24 may also comprise one or more sensors configured to detect the presence of the appliance 12 and ensure that the ultraviolet light source 18 is activatable only when the appliance 12 is located in the sanitizing chamber and the housing is in the closed position.

Figure 6B:
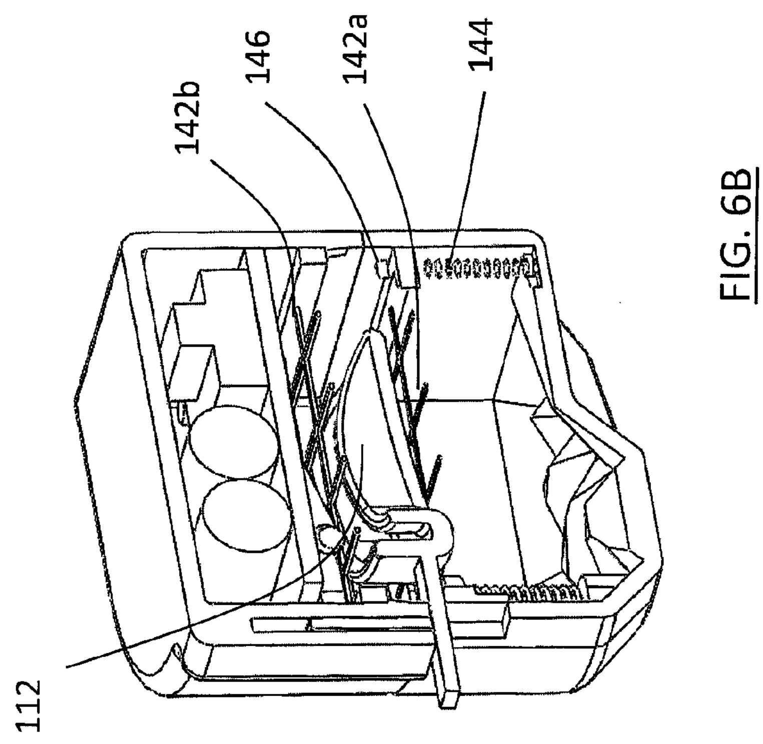
FIG. 6B is a sectional upper perspective view of the apparatus shown in FIG. 6A in a closed position with an oral appliance.
Figure 6A:
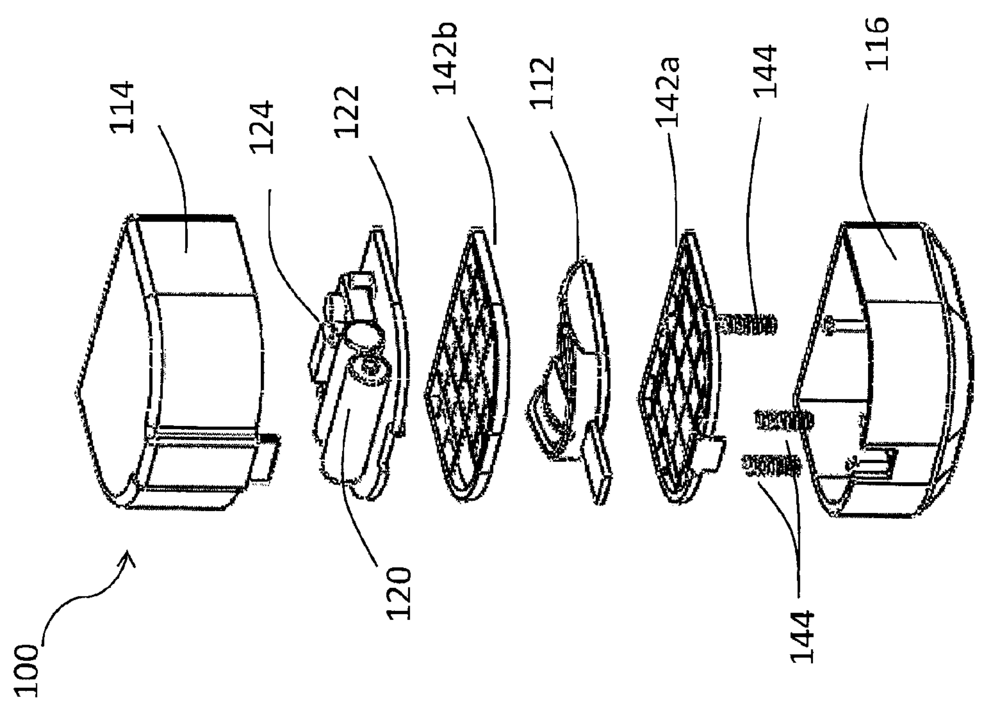
FIG. 6A is an exploded upper perspective view of another apparatus.

Referring to FIGS. 6A and 6B, another embodiment of an apparatus of the present invention is shown generally as 100. The apparatus 100 is shown in combination with an oral appliance 12. For the sake of convenience, the same reference numerals may be used herein to denote like features, elements, components, or portions.

The apparatus 100 includes an appliance suspension system for suspending the appliance 112 within the sanitizing chamber. The appliance suspension system may include a first platform 142*a* and a second platform 142*b* arranged on opposite sides of the appliance 112. The platforms 142*a*, 142*b* may be biased towards one another. For example, one of the platforms 142*a*, 142*b* may be fixed relative to the housing, and the other of the platforms 142*a*, 142*b* may be biased towards the one of the platforms 142*a*, 142*b* by springs 144. The springs 144 may be mounted to the lower portion 116 with posts 146. When the appliance 112 is inserted into housing and the housing is closed, the appliance 112 may be biased by springs 144 towards the upper platform 142*b* such that the platforms 142*a*, 142*b* engage the appliance 12 to hold the appliance 112 in a virtually central position within the sanitizing chamber.

Figure 7B:
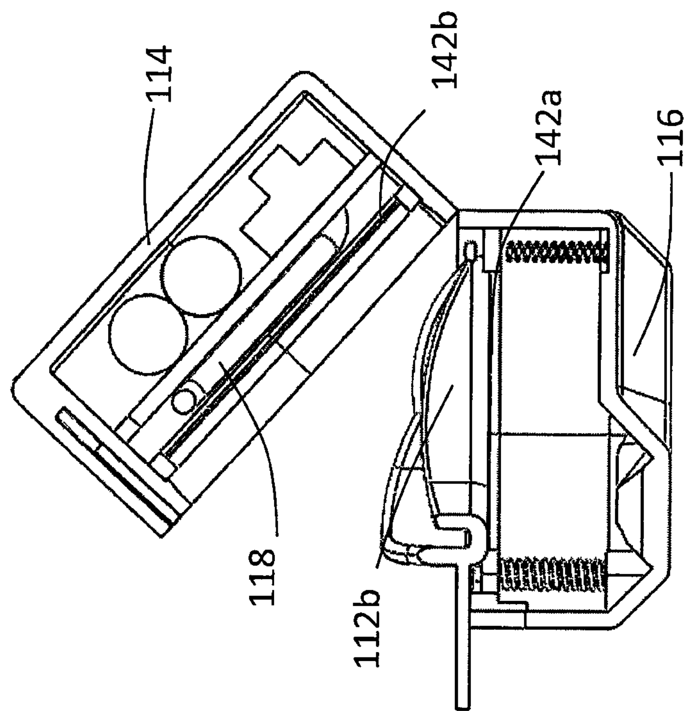
FIGS. 7A and 7B are sectional side views of the apparatus shown in FIG. 6A in an open position with differently sized oral appliances.
Figure 7A:
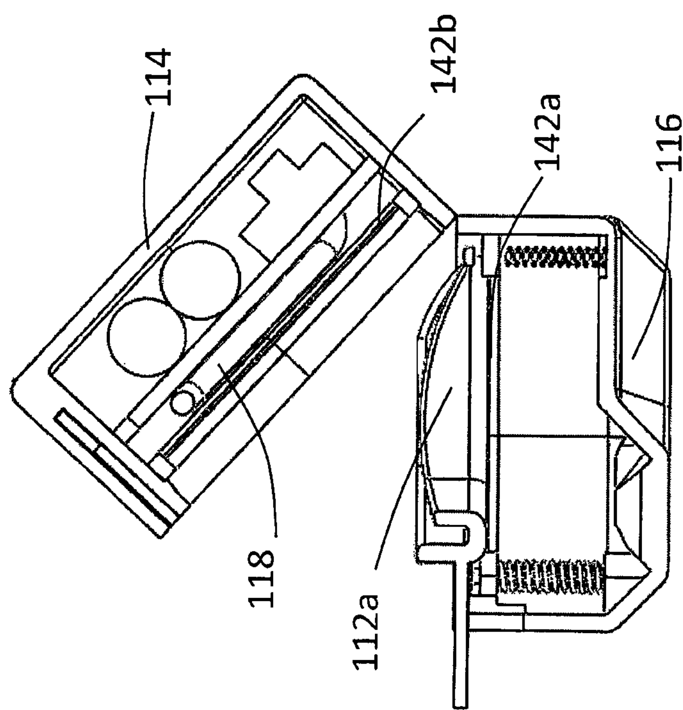
Figure 8B:
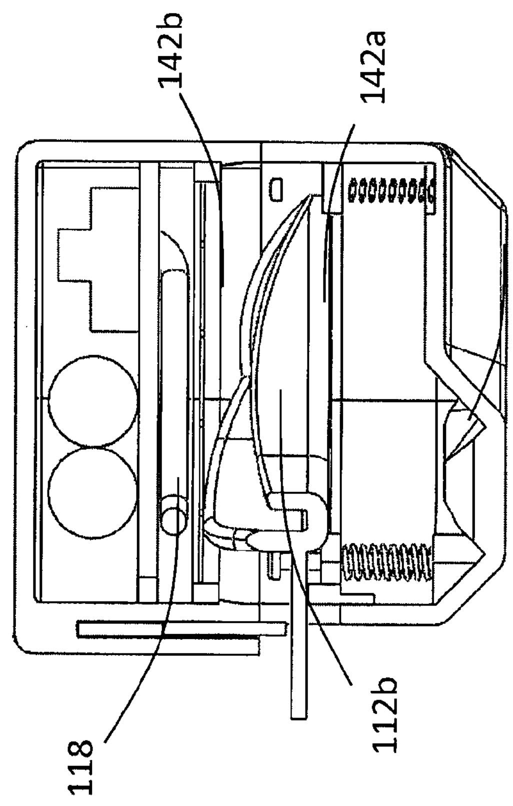
FIGS. 8A and 8B are sectional side views of the apparatus shown in FIG. 6A in a closed position with the differently sized oral appliances shown in FIGS. 7A and 7B.
Figure 8A:
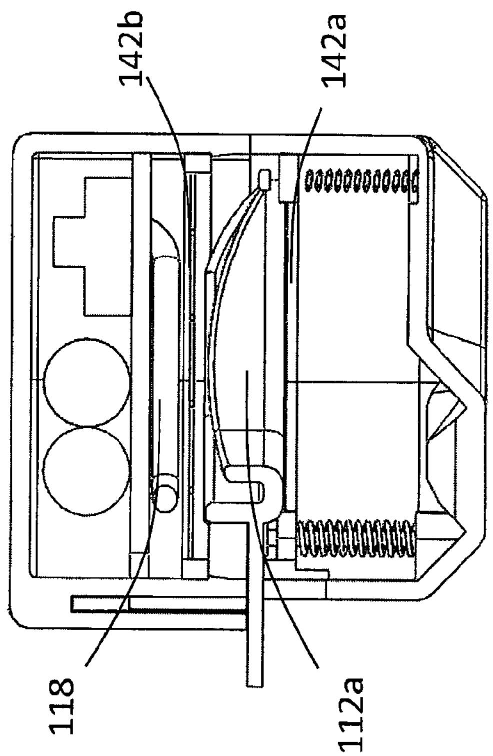
Figure 9B:
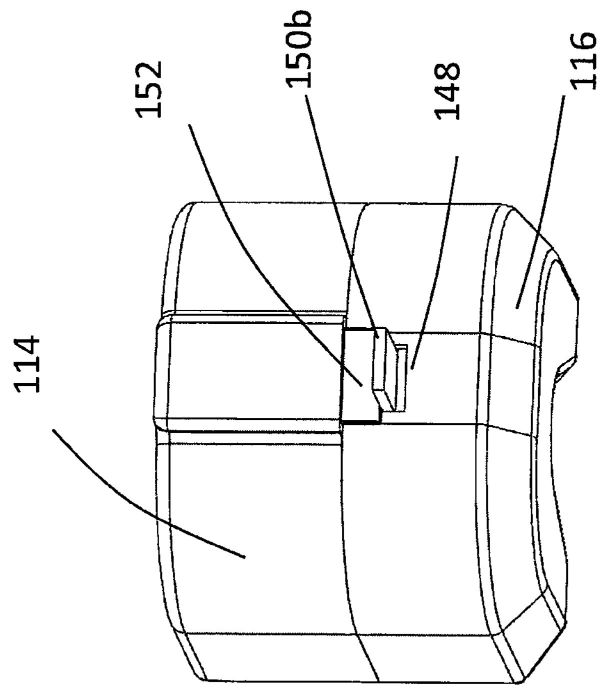
FIGS. 9A and 9B are front perspective views of the apparatus shown in FIG. 6A in a closed position with the differently sized oral appliances shown in FIGS. 7A and 7B.

The springs 144 may accommodate varying sized appliances 112. For example, the apparatus 100 is shown with a smaller appliance 112*a* in FIGS. 7A, 8A and 9A. The apparatus 100 is shown with a larger appliance 112*b* in FIGS. 7B, 8B and 9B. Distances between the appliance 112*a* and the ultraviolet light source 118 or the appliance 112*b* and the ultraviolet light source 118 may be close to the same, as may be maintained by the upper platform 142*b*. The springs may position the appliance virtually centrally in the apparatus to facilitate the surrounding of the appliance with sanitization means, such as for example ozone and/or ultraviolet light, to kill bacteria on the appliance. The springs may be formed of any material with requisite strength and flexibility to allow for the placement of the appliance within the platforms of the suspension system, and the positioning of the suspension system virtually centrally within the sanitization chamber. As shown in FIGS. 15A and 15B, springs 344, such as coil springs, may be utilized. Alternatively, as shown in FIG. 13, a resistance means 383, which may be a plastic spring, may be utilized as an alternative to a spring. A skilled reader will recognize the wide range of resistance means and springs that may be applied in embodiments of the present invention and further recognize that the choice of resistance means and/or spring may relate to the firmness of the material utilized to form the first platform.

The platforms 142*a*, 142*b* may also each include a mesh-like structure having a substantially open surface to allow light and/or gas to pass therethrough. For example, the mesh-like structure may have more than 80% open space along a particular section, or more than 90% open space along a particular section. A skilled reader will recognize that the mesh-like structure may have many variations on the open space incorporated therein. The platforms 142*a*, 142*b* may be adapted to hold the appliance 112 with minimal or little contact between the platforms 142*a*, 142*b* and the appliance 112. Minimal or little contact between the platforms 142*a*, 142*b* and the appliance 112 may ensure adequate exposure of the appliance 112 to ultraviolet light and/or ozone emitted by the ultraviolet light source 118. The platforms 142*a*, 142*b* may also be removable from the housing to allow cleaning or replacement of either or both of the platforms.

Figure 9A:
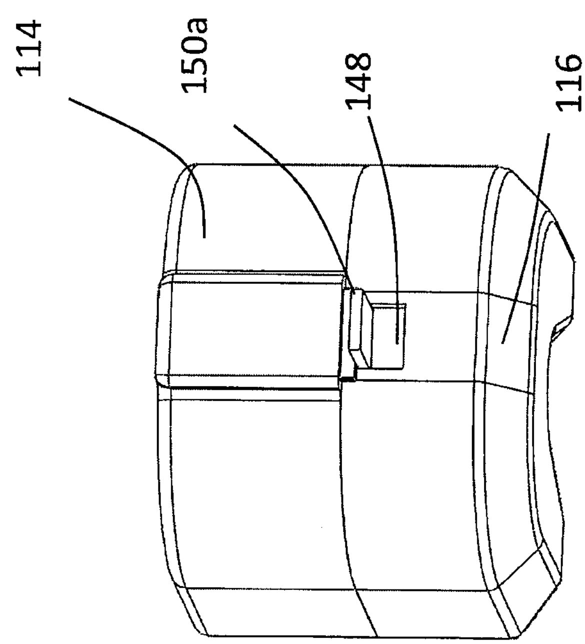
Figure 10B:
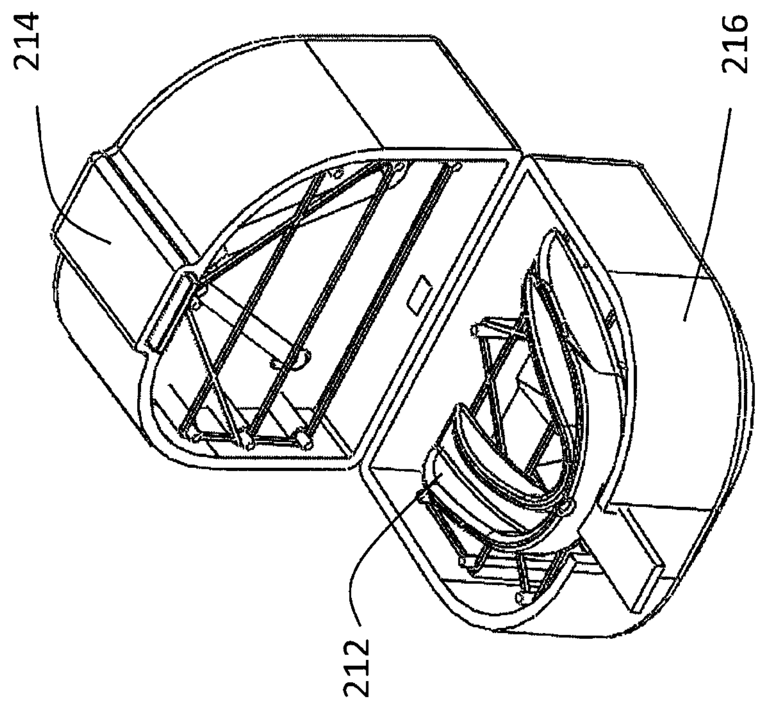
FIGS. 10A and 10B are upper perspective views of another apparatus in an open position without and with an oral appliance, respectively.
Figure 10A:
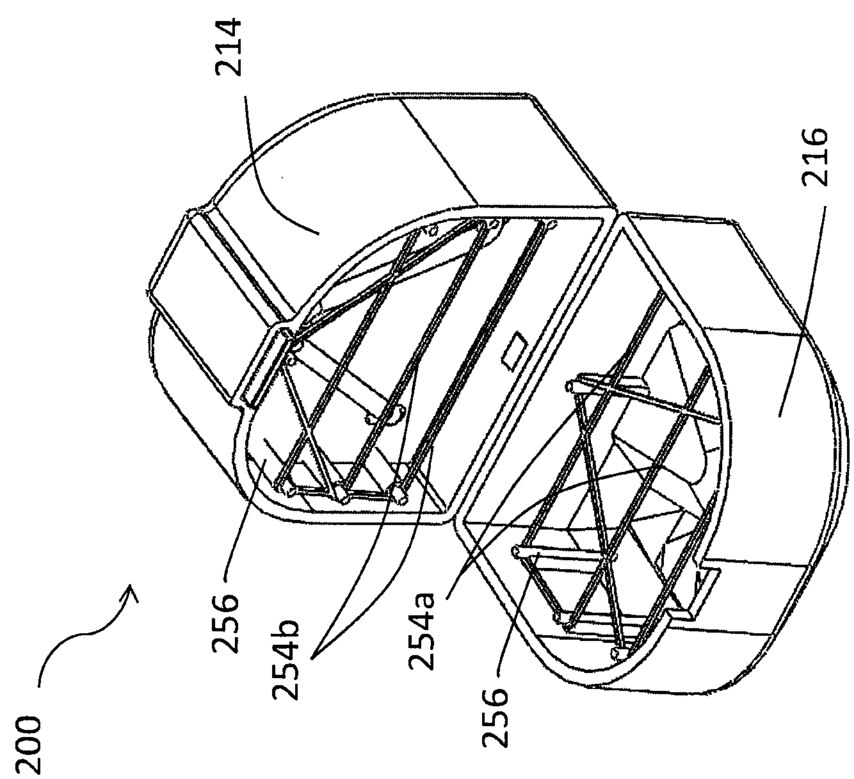
Figure 11B:
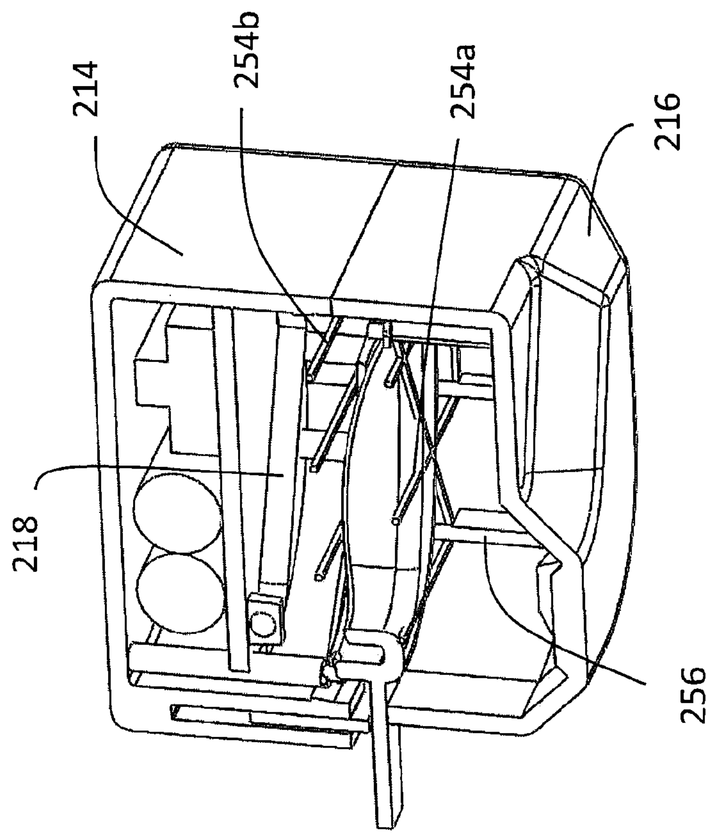
FIG. 11B is a sectional lower perspective view of the apparatus shown in FIGS. 10A and 10B in a closed position with an oral appliance.
Figure 11A:
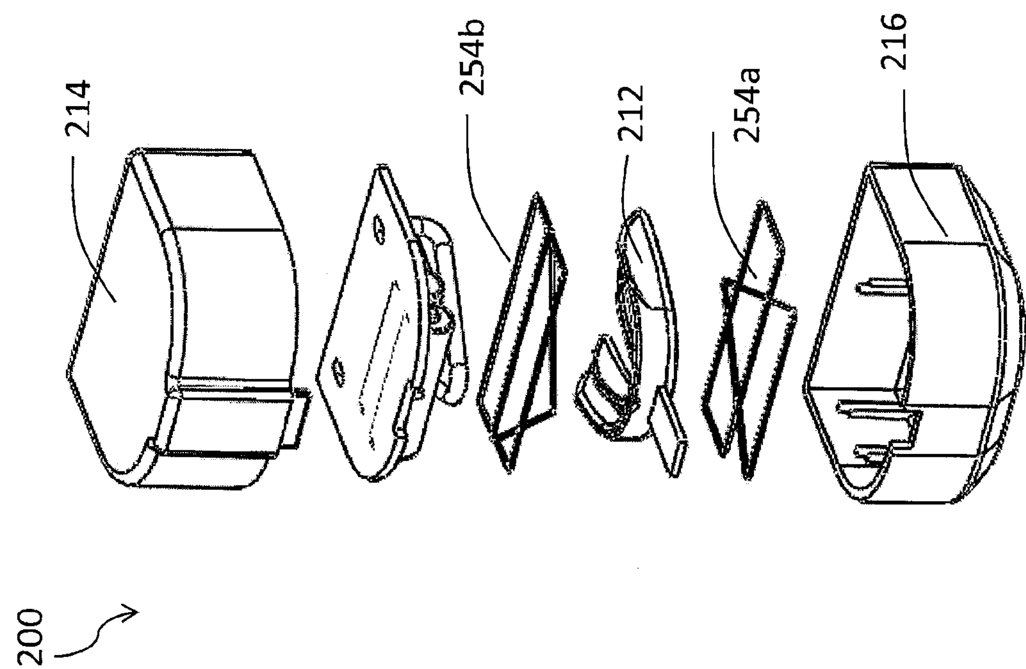
FIG. 11A is an exploded upper perspective view of the apparatus shown in FIGS. 10A and 10B.

Referring to FIGS. 9A and 913, the housing may include a gap 148 when in the closed position. The gap may be sized to accommodate a mouth guard tether 150*a* or 150*b*. Mouth guard tethers 150*a* or 150*b* may be of a size that corresponds with the size of an appliance, for example such as a smaller appliance 112*a* and a larger appliance 112*b*. A spring-loaded tab 152 may be provided for sealing the gap 148. In particular, the spring-loaded tab 152 may emerge from the upper portion 114 to close the 148 gap created when the larger appliance 112*b* depresses the lower platform 142*a* downwardly. Sections of the portions 114, 116 surrounding the gap 148 may be formed of a flexible material to accommodate wider tethers.

Referring to FIGS. 9A, 9B, 10A and 11B, another embodiment of an apparatus of the present invention is shown generally as 200. The apparatus 200 is shown in combination with an oral appliance 212. The apparatus 200 may include an appliance suspension system including a first platform 254*a* and a second platform 254*b* arranged on opposite sides of the appliance 212. The platforms 254*a*, 254*b* may be formed of elastic elements and mounted to the upper and lower portions 214, 216 by supports 256.

When the appliance 212 is inserted into the housing and the housing is closed, the platforms 254*a*, 254*b* may conform to the appliance 212 to hold the appliance 112 in a virtually central position within the sanitizing chamber. The platforms 254*a*, 254*b* may be adapted to hold the appliance 212 with minimal or little contact between the platforms 254*a*, 254*b* and the appliance 212. Minimal or little contact between the platforms 254*a*, 254*b* and the appliance 212 may ensure adequate exposure of the appliance 212 to ultraviolet light and/or ozone emitted by the ultraviolet light source 218. The platforms 254*a*, 254*b* may be removable and/or replaceable from the housing to allow for cleaning or replacement of one or both of the platforms.

A skilled reader will recognize that a variety of methods of use of the apparatus may be applied in the present invention. A user may open the apparatus and insert an oral appliance between the platforms. Upon closing the apparatus a sensor may sense the presence of the oral appliance. In one embodiment the control circuitry may include an automatic "on" feature, whereby a sanitization means, such as an ultraviolet light, may be turned on and activated when the apparatus is closed with an oral appliance inside. This automatic "on" feature may further be supported by a timer, so that the sanitization means will be emitted which the ultraviolet light is activated during a set period of time. Once that period of time is ended, the control circuitry may cause the sanitization means to be automatically shut-off and the ultraviolet light is thereby deactivated. At this point the user may open the apparatus and remove a sanitized oral appliance.

Another method applicable to the present invention is that a user may open the apparatus and insert an oral appliance between the platforms. The user may close the apparatus and then apply force to a manual switch for the purpose of indicating to the control circuitry that the sanitization means should be turned on. A user may further apply force to the manual switch to indicate to the control circuitry that the sanitization means should be turned off. In this manner the user may control the length of time that sanitization occurs within the sanitization chamber. Alternatively, the control circuitry may incorporate a timer, whereby upon the control circuitry turning the sanitization means on, the sanitization means will be emitted during a set period of time. Once that period of time is ended, the control circuitry may cause the sanitization means to be automatically shut-off.

A user may refer to an indicator light to determine if the sanitization means is turned "on" or "off". Additionally, a user may cause the sanitization means to be turned "off" by opening the apparatus.

Terms such as upper, lower, up, down, top, bottom, etc., may be used in this disclosure for the sake of clarity and relate to the position of the various components according to the illustrated examples. The teachings herein are not intended to be limited to particular orientations of the components and various orientations are possible.

In one embodiment of the present invention an apparatus for sanitizing an oral appliance, may comprise: a housing movable between open and closed positions, the housing in the open position allowing insertion of the oral appliance, the housing in the closed position defining a sanitizing chamber; an oral appliance suspension system; at least one ultraviolet light source capable of emitting one or more sanitization means within the sanitization chamber; and at least one power source for powering the at least one ultraviolet light source.

This embodiment may include an ultraviolet light source that emits one or more of ultraviolet light or ozone gas in the sanitizing chamber as the one or more sanitization means.

This embodiment of the present invention may further include an appliance suspension system that may comprise a first platform for holding the oral appliance in a virtually central position within the sanitizing chamber when the housing is in the closed position, whereby the appliance suspension system facilitates virtually uninhibited access to the oral appliance by the one or more sanitization means to ensure all over sanitization of the oral appliance.

The first platform may comprise a substantially open surface adapted to allow the one or more sanitization means to pass therethrough.

In this embodiment of the present invention the appliance suspension system may comprise opposing first and second platforms for holding the appliance in a virtually central position within the sanitizing chamber when the housing is in the closed position, whereby the appliance suspension system facilitates virtually uninhibited access to the oral appliance by the one or more sanitization means to ensure all over sanitization of the oral appliance.

The first and second platforms may each comprise a substantially open surface adapted to allow the one or more sanitization means to pass therethrough.

At least one of the first and second platforms may be flexible for accommodating appliances of varying sizes.

At least one of the first and second platforms may comprise elastic members.

The first and second platforms may be biased towards one another.

The position of one of the first or second platforms may be fixed relative to the housing, and the other of the first or second platforms is spring biased towards the one of the first or second platforms.

The first and second platforms may be removable from the housing.

The present invention may further include at least one power source that may be connected to a control circuitry, wherein the control circuitry may connect the power source to the ultraviolet light source to activate the ultraviolet light source if one or more of the following occurs: the housing is in the closed position and a manual switch is engaged; and the housing is in the closed position during a preset activation time; and wherein the control circuitry may disconnect the power source from the at least one ultraviolet light source to deactivate the ultraviolet light source at one or more of the following: when the housing is in the open position; after the duration of a preset activation time; and after the manual switch is disengaged for activating the ultraviolet light source.

The present invention may also include one or more indicators connected to the control circuitry for indicating if the ultraviolet light source transitions from activated to deactivated states, wherein the one or more indicators may be one or more of the following: one or more indicator lights; and one or more audible indicators.

At least one ultraviolet light source may be protected from contact with other items by a shield.

The housing may comprise an upper portion and a lower portion, the upper portion and the lower portion movable to define the open and closed positions.

The upper and lower portions may be connected by a hinge, and further comprise a detent or fastener for maintaining the upper and lower portions in the closed position.

The ultraviolet light source may be secured to the upper portion.

The ultraviolet light source may be secured to a divider and the divider is secured to the upper portion, and wherein the power source and a control circuitry are disposed generally between the divider and the upper portion.

The present invention may also comprise a status light for indicating if the ultraviolet light source is activated.

The power source may comprise one or more of the following: a plug for connection to a domestic power socket; at least one battery; and one or more solar panels.

The power source may comprise at least one battery further comprises a battery light for indicating power status of the at least one battery.

The housing may include a gap sized to accommodate a mouth guard tether when in the closed position.

A spring-loaded tab may be included for sealing the gap when the housing is in the closed position.

Another embodiment of the present invention may be an apparatus for sanitizing an oral appliance, characterized in that it comprises: a housing movable between open and closed positions, the housing in the open position allowing insertion of the appliance, the housing in the closed position defining a sanitizing chamber; an appliance suspension system; at least one ultraviolet light source capable of emitting one or more sanitization means within the sanitization chamber; at least one power source for powering the ultraviolet light source; and at least one reflective interior surface provided on or in the sanitizing chamber, whereby the one or more sanitization means may be reflected within the sanitizing chamber.

One or more of the at least one reflective interior surface may facilitate scattering of the one or more sanitization means.

The one or more of the at least one reflective interior surface may comprise a polyhedral surface.

The one or more of the at least one reflective interior surface may comprise a curvilinear surface.

The at least one reflective interior surface may comprise a first reflective interior surface proximate to the at least one ultraviolet light source, and a second reflective interior surface spaced apart from the first reflective interior surface.

The first and second reflective interior surfaces may be provided on opposing sides of the sanitizing chamber.

The second reflective interior surface may be provided on a removable tray.

The appliance suspension system may comprise opposing first and second platforms for holding the appliance in a virtually central position within the sanitizing chamber when the housing is in the closed position, whereby the appliance suspension system facilitates virtually uninhibited access to the oral appliance by the one or more sanitization means to ensure all over sanitization of the oral appliance.

The at least one ultraviolet light source may emit one or more of ultraviolet light or ozone gas in the sanitizing chamber as the one or more sanitization means.

The at least one power source may be connected to a control circuitry, wherein the control circuitry disconnects the power source from the at least one ultraviolet light source to deactivate the ultraviolet light source when the housing is in the open position.

The at least one ultraviolet light source may be protected from contact with other items by a shield.

Yet another embodiment of the present invention may be an apparatus for sanitizing an oral appliance, the apparatus comprising: a housing movable between open and closed positions, the housing in the open position allowing insertion of the appliance, the housing in the closed position defining a sanitizing chamber; an ultraviolet light source disposed within the housing for emitting ultraviolet light and ozone gas within the sanitizing chamber; and at least one power source for powering the ultraviolet light source and the ozone source.

The sanitization chamber may incorporate an appliance suspension system comprising opposing first and second platforms for holding the appliance in a virtually central position within the sanitizing chamber when the housing is in the closed position, whereby the appliance suspension system facilitates virtually uninhibited access to the oral appliance by one or more of the ozone gas and the ultraviolet light to ensure all over sanitization of the oral appliance.

The ultraviolet light source may be adapted to emit UV light having a wavelength of about 100 to about 280 nanometers, or about 170 to about 260 nanometers, or about 175 to about 220 nanometers, or about 180 to 190 manometers.

The ultraviolet light source may comprise at least one UVC bulb.

The at least one power source may be connected to a control circuitry, wherein the control circuitry disconnects the power source from the at least one ultraviolet light source to deactivate the ultraviolet light source when the housing is in the open position.

The at least one ultraviolet light source may be protected from contact with other items by a shield.

Still another embodiment of the present invention may be a method of utilizing an apparatus to sanitize an oral appliance, characterized in that it comprises the steps of: manipulating a housing of the apparatus to an open position to facilitate access to an oral appliance suspension system; placing the oral appliance in the oral appliance suspension system; manipulating the housing of the apparatus to a closed position, whereby the oral appliance is positioned virtually centrally within a sanitization chamber that is defined within the housing when the apparatus is in the closed position; activating at least one ultraviolet light source to emit one or more sanitization means within the sanitization chamber; sanitizing the oral appliance by application of the sanitization means to the oral appliance; deactivating the at least one ultraviolet light source by one of the following: manipulating the housing of the apparatus to an open position; terminating a duration of a preset activation time; disengaging a manual switch connected to a control circuitry, whereby the at least one ultraviolet light source is deactivated; and disengaging a power source from providing power to the at least one ultraviolet light source.

It is anticipated that those having ordinary skill in this art may make various modification to the apparatuses and methods disclosed herein to produce modified apparatuses and methods that fall within the scope of the present invention as defined by the following claims.

It will be appreciated by those skilled in the art that other variations of the embodiments described herein may also be practiced without departing from the scope of the invention. Other modifications are therefore possible. For example, the calendar may be a type other than a wall calendar, for example a bound calendar, a perpetual calendar, or a wheel-displayed calendar.

We claim:

1. An apparatus for sanitizing an oral appliance comprising:

(a) a housing movable between open and closed positions, the housing in the open position allowing insertion of the oral appliance, the housing in the closed position defining a sanitizing chamber;

(b) an oral appliance suspension system that incorporates one or more openings therein and is operable to position the oral appliance to be free of contact with any of the following: the housing, at least one ultraviolet light source, and surfaces within the housing other than the oral appliance suspension; and to provide virtually uninhibited access to the oral appliance by one or more sanitization means when the apparatus is resting at any angle;

(c) the at least one ultraviolet light source capable of emitting the one or more sanitization means within the sanitization chamber; and (d) at least one power source for powering the at least one ultraviolet light source.

2. The apparatus of claim 1, wherein the at least one ultraviolet light source emits one or more of ultraviolet light or ozone gas in the sanitizing chamber as the one or more sanitization means, and said at least one ultraviolet light source is protected from contact with other items by a shield, and the apparatus is easily transportable.

3. The apparatus of claim 1, wherein the oral appliance suspension system is operable during transport of the apparatus, and comprises one or more of the following:

(a) a first platform for holding the oral appliance in a virtually central position within the sanitizing chamber when the housing is in the closed position; or (b) opposing first and second platforms for holding the appliance in a virtually central position within the sanitizing chamber when the housing is in the closed position, whereby the oral appliance suspension system provides for all over sanitization of the oral appliance.

4. The apparatus of claim 3, wherein at least one of the first platform; or the first and second platform; comprises a substantially open support formed of a mesh-like structure that allows the one or more sanitization means to directly access virtually all of the oral appliance.

5. The apparatus of claim 3, wherein at least one of the first and second platforms is flexible for accommodating appliances of varying sizes.

6. The apparatus of claim 3, wherein at least one of the first and second platforms comprises elastic members.

7. The apparatus of claim 3, wherein the first and second platforms are in accordance with one of the following:

(a) the position of one of the first or second platforms is fixed relative to the housing, and the other of the first or second platforms is spring biased towards the one of the first or second platforms; or (b) the first and second platforms are biased towards one another.

8. The apparatus of claim 3, wherein the first and second platforms are removable from the housing.

9. The apparatus of claim 1, wherein the at east one power source is connected to a control circuitry, wherein the control circuitry connects the power source to the ultraviolet light source to activate the ultraviolet light source if one or more of the following occurs:

(a) the housing is in the closed position and a manual switch is engaged; and (b) the housing is in the closed position during a preset activation time; and wherein the control circuitry disconnects the power source from the at least one ultraviolet light source to deactivate the ultraviolet light source at one or more of the following:

(c) when the housing is in the open position;

(d) after the duration of a preset activation time; and (e) after the manual switch is disengaged for activating the ultraviolet light source.

10. The apparatus of claim 9, further comprising one or more indicators connected to the control circuitry for indicating if the ultraviolet light source transitions from activated to deactivated states, wherein the one or more indicators may be one or more of the following:

(a) one or more indicator lights; and (b) one or more audible indicators.

11. The apparatus of claim 1, wherein the housing comprises an upper portion and a lower portion that are one or more of the following:

(a) movable to define the open and closed positions; and (b) connected by a hinge, and further comprise a detent or fastener for maintaining the upper and lower portions in the closed position.

12. The apparatus of claim 11, wherein the ultraviolet light source is secured to the upper portion, and said ultraviolet light source is secured to a divider and the divider is secured to the upper portion, and wherein the power source and a control circuitry are disposed generally between the divider and the upper portion.

13. The apparatus of claim 1, further comprising a status light for indicating if the ultraviolet light source is activated.

14. The apparatus of claim 1, wherein the housing includes a gap sized to accommodate a mouth guard tether when in the closed position and a spring-loaded tab for sealing the gap when the housing is in the closed position.

15. An apparatus for sanitizing an oral appliance comprising:

(a) a housing movable between open and closed positions, the housing in the open position allowing insertion of the appliance, the housing in the closed position defining a sanitizing chamber;

(b) an oral appliance suspension system that incorporates one or more openings therein and is operable to position the oral appliance to be free of contact with any of the following: the housing, at least one ultraviolet light source, and surfaces within the housing other than the oral appliance suspension; and to provide virtually uninhibited access to the oral appliance by one or more sanitization means when the apparatus is resting at any angle;

(c) the at least one ultraviolet light source capable of emitting the one or more sanitization means within the sanitization chamber;

(d) at least one power source for powering the ultraviolet light source; and (e) at least one reflective interior surface provided on or in the sanitizing chamber, whereby the one or more sanitization means may be reflected within the sanitizing chamber.

16. The apparatus of claim 15, wherein one or more of the at least one reflective interior surface facilitates scattering of the one or more sanitization means, said at least one reflective interior surface comprising at least one of the following:

(a) a polyhedral surface;

(b) a curvilinear surface;

(c) a first reflective interior surface proximate to the at least one ultraviolet light source, and a second reflective interior surface spaced apart from the first reflective interior surface, said first and second reflective surfaces being provided on one of the following:

(i) opposing sides of the sanitizing chamber; or (ii) a removable tray.

17. The apparatus of claim 15, wherein the ultraviolet light source is adapted to emit UV light having a wavelength of about 100 to about 280 nanometers, or about 170 to about 260 nanometers, or about 175 to about 220 nanometers, or about 180 to 190 manometers.

18. The apparatus of claim 15, wherein the ultraviolet light source comprises at least one UVC bulb.

19. A method of utilizing an apparatus to sanitize an oral appliance, comprising the steps of:

(a) manipulating a housing of the apparatus to an open position to facilitate access to an oral appliance suspension system;

(b) placing the oral appliance in the oral appliance suspension system that incorporates one or more open sections and is operable to position the oral appliance to be free of contact with any of the following: the housing, at least one ultraviolet light source, and surfaces within the housing other than the oral appliance suspension; and to provide virtually uninhibited access to the oral appliance by or more sanitization means when the apparatus is resting at any angle;

(c) manipulating the housing of the apparatus to a closed position, whereby the oral appliance is positioned in accordance with the oral appliance suspension system virtually centrally within a sanitization chamber that is defined within the housing when the apparatus is in the closed position;

(d) activating the at least one ultraviolet light source to emit the one or more sanitization means within the sanitization chamber;

(e) sanitizing the oral appliance by application of the sanitization means to the oral appliance;

(f) deactivating the at least one ultraviolet light source by one of the following:

(i) manipulating the housing of the apparatus to an open position;

(ii) terminating a duration of a preset activation time;

(iii) disengaging a manual switch connected to a control circuitry, whereby the at least one ultraviolet light source is deactivated; and (iv) disengaging a power source from providing power to the at least one ultraviolet light source.

* * * * *